United States Patent [19]

Sugiura et al.

[11] Patent Number: 5,061,719
[45] Date of Patent: Oct. 29, 1991

[54] AZOLIDINE DERIVATIVES, PROCESS FOR PREPARING THE SAME AND AGRICULTURAL AND HORTICULTURAL FUNGICIDE

[75] Inventors: Hisao Sugiura; Toshinobu Tanaka; Takashi Nishimura; Shuji Yokoyama, all of Ube, Japan

[73] Assignee: Ube Industries, Ltd., Ube, Japan

[21] Appl. No.: 556,948

[22] Filed: Jul. 20, 1990

[30] Foreign Application Priority Data

Aug. 8, 1989 [JP] Japan .................................. 1-203732

[51] Int. Cl.$^5$ .................... A01N 43/90; C07D 413/02
[52] U.S. Cl. ................................ 514/374; 514/340; 514/342; 514/365; 546/275; 546/277; 548/200; 548/215; 548/216
[58] Field of Search ................ 548/216, 215; 514/374

[56] References Cited

U.S. PATENT DOCUMENTS

| | | | |
|---|---|---|---|
| 3,472,864 | 10/1969 | Henry | 548/215 |
| 3,825,555 | 7/1974 | Lajiness | 548/216 |
| 4,528,195 | 7/1985 | Thorogood | 514/374 |
| 4,708,960 | 11/1987 | Renzea et al. | 548/341 |
| 4,752,607 | 6/1988 | Daum et al. | 514/374 |
| 4,863,947 | 9/1989 | Jacobsen | 514/374 |
| 4,889,864 | 12/1989 | Ehrhardt et al. | 514/526 |

FOREIGN PATENT DOCUMENTS 0021238 2/1977 Japan .................................. 514/374

Primary Examiner—Donald G. Daus
Attorney, Agent, or Firm—Frishauf, Holtz, Goodman & Woodward

[57] ABSTRACT

There are disclosed an azolidine derivative represented by the formula:

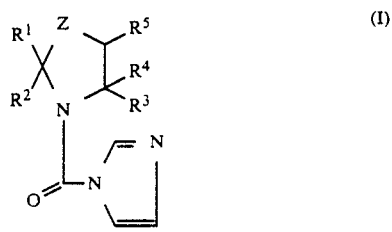

wherein $R^1$ represents a hydrogen atom, an alkyl group or a cycloalkyl group; $R^2$ represents a hydrogen atom, an alkyl group, an alkenyl group, an alkynyl group, an alkoxyalkyl group, an alkenyloxyalkyl group, an alkylthioalkyl group, an alkoxycarbonyl group, a furyl group or a thienyl group, or a phenylalkyl group, a phenoxyalkyl group, a phenylthioalkyl group, a phenylalkyloxyalkyl group, a pyridyloxyalkyl group, a phenoxyphenoxyalkyl group, a benzyloxyphenoxyalkyl group or a pyridyloxyphenoxyalkyl group, or $R^1$ and $R^2$ may be combined with each other with carbon atoms bonded thereto to form a group represented by the formula:

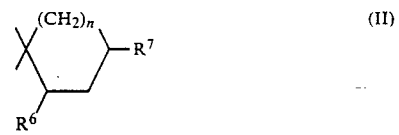

where $R^6$ represents a hydrogen atom, a halogen atom or a lower alkyl group; $R^7$ represents a hydrogen atom, an alkyl group, an alkenyl group, an alkoxy group, an alkenyloxy group or an alkylthio group, or a phenyl group, a phenoxy group, a benzyloxy group or a pyridylthio group; n is an integer of 1 to 3;

$R^3$ represents a hydrogen atom or a lower alkyl group;

$R^4$ represents a hydrogen atom, a lower alkyl group, a phenyl group or a benzyl group; or $R^3$ and $R^4$ may be combined with each other with carbon atoms bonded thereto to form a group represented by the formula:

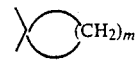

where m is an integer of 4 or 5;

$R^5$ represents a hydrogen atom, a lower alkyl group or a phenyl group, or $R^4$ and $R^5$ may be combined with each other with carbon atoms bonded thereto to form a group represented by the formula:

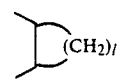

where l represents an integer of 3 or 4;

and Z represents an oxygen atom or a sulfur atom, a process for producing the same and an agricultural and horticultural fungicide containing the same as an active ingredient.

16 Claims, No Drawings

AZOLIDINE DERIVATIVES, PROCESS FOR PREPARING THE SAME AND AGRICULTURAL AND HORTICULTURAL FUNGICIDE

BACKGROUND OF THE INVENTION

This invention relates to azolidine derivatives, a process for preparing the same and an agricultural and horticultural fungicide containing the same as active ingredients.

The azolidine derivatives of the present invention are quite novel compounds as an agricultural and horticultural fungicide and similar compounds have never been known.

SUMMARY OF THE INVENTION

An object of the present invention is to provide a novel azolidine derivative which is effective as an agricultural and horticultural fungicide.

That is, the azolidine derivatives of the present invention have the following formula:

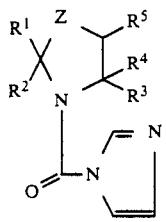
(I)

wherein $R^1$ represents a hydrogen atom, an alkyl group having 1 to 10 carbon atoms or a cycloalkyl group; $R^2$ represents a hydrogen atom, an alkyl group having 1 to 18 carbon atoms, an alkenyl group, an alkynyl group, an alkoxyalkyl group, an alkenyloxyalkyl group, an alkylthioalkyl group, an alkoxycarbonyl group, a furyl group or a thienyl group, or a phenylalkyl group, a phenoxyalkyl group, a phenylthioalkyl group, a phenylalkyloxyalkyl group, a pyridyloxyalkyl group, a phenoxyphenoxyalkyl group, a benzyloxyphenoxyalkyl group or a pyridyloxyphenoxyalkyl group, those of phenyl rings or pyridine rings may be substituted by a halogen atom, an alkyl group, an alkoxy group, a haloalkyl group or a haloalkoxy group; or $R^1$ and $R_2$ may be combined with each other with carbon atoms bonded thereto to form a group represented by the formula:

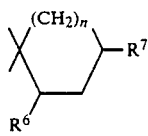
(II)

where $R^6$ represents a hydrogen atom, a halogen atom or a lower alkyl group; $R^7$ represents a hydrogen atom, an alkyl group, an alkenyl group, an alkoxy group, an alkenyloxy group or an alkylthio group, or a phenyl group, a phenoxy group, a benzyloxy group or a pyridylthio group, those of phenyl rings or a pyridine ring may be substituted by a halogen atom, an alkyl group, an alkoxy group or a haloalkyl group; n is an integer of 1 to 3;
$R^3$ represents a hydrogen atom or a lower alkyl group;
$R^4$ represents a hydrogen atom, a lower alkyl group, a phenyl group or a benzyl group; or $R^3$ and $R^4$ may be combined with each other with carbon atoms bonded thereto to form a group represented by the formula:

where m is an integer of 4 or 5;
$R^5$ represents a hydrogen atom, a lower alkyl group or a phenyl group, or $R^4$ and $R^5$ may be combined with each other with carbon atoms bonded thereto to form a group represented by the formula:

where l represents an integer of 3 or 4;
and Z represents an oxygen atom or a sulfur atom.

In the formula (I), the alkyl group represented by $R^1$ includes an alkyl group having 1 to 10 carbon atoms such as a methyl group, an ethyl group, a propyl group, a butyl group, a pentyl group, a hexyl group, a heptyl group, an octyl group, a nonyl group and a decyl group, and among them, a methyl group is particularly preferred. The cycloalkyl group includes a cycloalkyl group having 3 to 6 carbon atoms such as a cyclopropyl group, a cyclopentyl group and a cyclohexyl group.

The alkyl group represented by $R^2$ includes, in addition to the alkyl groups exemplified in the above $R^1$, straight or branched alkyl groups having 1 to 18 carbon atoms such as an undecyl group, a dodecyl group, a tetradecyl group, a hexadecyl group, an octadecyl group, a 1-ethylpentyl group and a 3-methylhexyl group, and among them, straight alkyl groups having 5 to 12 carbon atoms are particularly preferred. The alkenyl group may include an alkenyl group having 1 to 8 carbon atoms such as an allyl group, a 2-butenyl group, a 2-pentenyl group and a 1-butyl-2-butenyl group. The alkynyl group may include a 2-propynyl group. The alkoxyalkyl group may include a methoxyethyl group, an ethoxymethyl group and a dodecyloxymethyl group. The alkenyloxyalkyl group may include an all, allyloxyethyl group. The alkylthioalkyl group may include a methylthioethyl group and a dodecylthiomethyl group. The alkoxycarbonyl group may include a methoxycarbonyl group and an ethoxycarbonyl group. Alkyl portions of the phenylalkyl group, phenoxyalkyl group, phenylthioalkyl group, phenylalkyloxyalkyl group, pyridyloxyalkyl group, phenoxyphenoxyalkyl group, benzyloxyphenoxyalkyl group and pyridyloxyphenoxyalkyl group are alkyl groups having 1 to 5 carbon atoms, and the $C_3$ alkyl group is particularly preferred in the phenylalkyl group. As the halogen atom which is a substituent for a phenyl ring or a pyridine ring, there may be mentioned a chlorine atom, a bromine atom, a fluorine atom and an iodine atom, and the alkyl group may include an alkyl group having 1 to 6 carbon atoms such as a methyl group, an ethyl group, a propyl group, an isopropyl group, a butyl group, a pentyl group and a hexyl group. The alkoxy group may include an alkoxy group having 1 to 4 carbon atoms such as a methoxy group, an ethoxy group, a propyloxy group, an isopropyloxy group and a butyloxy group. The haloalkyl group may include a trifluoromethyl group. The haloalkoxy group may include a 2,2,2-trifluoroethoxy group.

As the halogen atom for $R^6$, a chlorine atom is particularly preferred, and as the lower alkyl group, a methyl group may be mentioned.

As the alkyl group for $R^7$, there may be mentioned an alkyl group having 1 to 6 carbon atoms such as a methyl group, an ethyl group, a propyl group, a butyl group, a pentyl group and a hexyl group. The alkenyl group may include an allyl group and a 2-butenyl group. The alkoxy group may include an alkoxy group having 1 to 6 carbon atoms such as a methoxy group, an ethoxy group, a propyloxy group, a butyloxy group, a pentyloxy group and a hexyloxy group. The alkenyloxy group may include an allyloxy group. The alkylthio group may include a methylthio group, an ethylthio group and a pentylthio group. A substituent for a phenyl ring or a pyridine ring of the phenyl group, phenoxy group, benzyloxy group and pyridyloxy group may include those substituents explained in the above $R^2$.

Preferred groups in the compound of the formula (I) are as follows: $R^1$ is a hydrogen atom or a methyl group. $R^2$ is a straight alkyl group having 5 to 12 carbon atoms, a phenylalkyl group in which the alkyl portion being 1 to 5 carbon atoms, particularly preferably a phenylalkyl group having chlorine or bromine atom at p-position of the phenyl group and having the alkyl portion with 3 carbon atoms, or a phenoxyalkyl group, and said phenyl group may be unsubstituted or substituted by a lower alkyl group or an alkoxy group. In the group of the formula (II) formed by combining $R^1$ and $R^2$ and carbon atoms bonded thereto, $R^6$ is a hydrogen atom or a chlorine atom, $R^7$ is a hydrogen atom, an alkyl group having 4 to 6 carbon atoms, an alkoxy group having 4 to 6 carbon atoms, an allyloxy group, or a phenyl group, a phenoxy group or a benzyl group which may be substituted by a halogen-atom. n is 2. $R^3$ and $R^4$ each are a methyl group, or

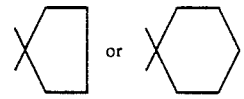

which is formed by combining $R^3$ and $R^4$ with carbon atoms bonded thereto. $R^5$ is a hydrogen atom. Z is an oxygen atom.

In Table 1, compounds contained in the formula (I) of the present invention will be exemplified.

TABLE 1

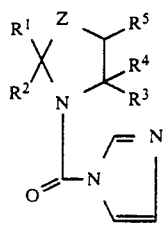 (I)

| Compound No. | $R^1$ | $R^2$ | $R^3$ | $R^4$ | $R^5$ | Z | Physical Property |
|---|---|---|---|---|---|---|---|
| 1 | H | $C_6H_{13}$-n | $CH_3$ | $CH_3$ | H | O | $n_D^{27}$ 1.4830 |
| 2 | H | $C_7H_{15}$-n | $CH_3$ | $CH_3$ | H | O | $n_D^{26}$ 1.4778 |
| 3 | H | $C_8H_{17}$-n | $CH_3$ | $CH_3$ | H | O | $n_D^{26}$ 1.4835 |
| 4 | H | $C_9H_{19}$-n | $CH_3$ | $CH_3$ | H | O | $n_D^{26}$ 1.4768 |
| 5 | H | $C_{10}H_{21}$-n | $CH_3$ | $CH_3$ | H | O | |
| 6 | H | $C_{11}H_{23}$-n | $CH_3$ | $CH_3$ | H | O | $n_D^{27}$ 1.4814 |
| 7 | H | (thienylmethyl) | $CH_3$ | $CH_3$ | H | O | $n_D^{26}$ 1.5103 |
| 8 | H | (furfuryl) | $CH_3$ | $CH_3$ | H | O | $n_D^{25}$ 1.4873 |
| 9 | H | —$CH(C_2H_5)C_4H_9$ | $CH_3$ | $CH_3$ | H | O | $n_D^{26}$ 1.4828 |
| 10 | H | —$(CH_2)_3$—phenyl | $CH_3$ | $CH_3$ | H | O | |
| 11 | $CH_3$ | $C_6H_{13}$-n | $CH_3$ | $CH_3$ | H | O | $n_D^{26}$ 1.4869 |
| 12 | $CH_3$ | $C_7H_{15}$-n | $CH_3$ | $CH_3$ | H | O | $n_D^{26}$ 1.4880 |
| 13 | $CH_3$ | $C_8H_{17}$-n | $CH_3$ | $CH_3$ | H | O | $n_D^{27}$ 1.4872 |
| 14 | $CH_3$ | $C_9H_{19}$-n | $CH_3$ | $CH_3$ | H | O | $n_D^{26}$ 1.4864 |
| 15 | $CH_3$ | $C_{10}H_{21}$-n | $CH_3$ | $CH_3$ | H | O | $n_D^{26}$ 1.4833 |
| 16 | $CH_3$ | $C_{12}H_{25}$-n | $CH_3$ | $CH_3$ | H | O | |
| 17 | $C_2H_5$ | $C_7H_{15}$-n | $CH_3$ | $CH_3$ | H | O | $n_D^{26}$ 1.4945 |
| 18 | $C_5H_{11}$-n | $C_5H_{11}$-n | $CH_3$ | $CH_3$ | H | O | $n_D^{27}$ 1.4902 |
| 19 | $C_7H_{15}$-n | $C_7H_{15}$-n | $CH_3$ | $CH_3$ | H | O | $n_D^{26}$ 1.4822 |

TABLE 1-continued $$\text{(I)}$$

| Compound No. | $R^1$ | $R^2$ | $R^3$ | $R^4$ | $R^5$ | Z | Physical Property |
|---|---|---|---|---|---|---|---|
| 20 | CH$_3$ | —(CH$_2$)$_4$—C$_6$H$_5$ | CH$_3$ | CH$_3$ | H | O | $n_D^{26}$ 1.5264 |
| 21 | CH$_3$ | —(CH$_2$)$_5$—C$_6$H$_5$ | CH$_3$ | CH$_3$ | H | O | $n_D^{20}$ 1.5103 |
| 22 | CH$_3$ | —(CH$_2$)$_3$—C$_6$H$_4$-4-Cl | CH$_3$ | CH$_3$ | H | O | $n_D^{20}$ 1.5196 |
| 23 | CH$_3$ | —(CH$_2$)$_3$—C$_6$H$_4$-4-Br | CH$_3$ | CH$_3$ | H | O | $n_D^{25}$ 1.5152 |
| 24 | CH$_3$ | —(CH$_2$)$_3$—C$_6$H$_4$-4-F | CH$_3$ | CH$_3$ | H | O | $n_D^{24}$ 1.5044 |
| 25 | CH$_3$ | —(CH$_2$)$_3$—C$_6$H$_3$-3,4-Cl$_2$ | CH$_3$ | CH$_3$ | H | O | $n_D^{24}$ 1.5182 |
| 26 | CH$_3$ | —(CH$_2$)$_3$—C$_6$H$_4$-4-CH$_3$ | CH$_3$ | CH$_3$ | H | O | $n_D^{24}$ 1.5096 |
| 27 | CH$_3$ | —(CH$_2$)$_3$—C$_6$H$_3$-2,4-Cl$_2$ | CH$_3$ | CH$_3$ | H | O | $n_D^{23}$ 1.5046 |
| 28 | CH$_3$ | —(CH$_2$)$_3$—C$_6$H$_4$-4-C$_2$H$_5$ | CH$_3$ | CH$_3$ | H | O | $n_D^{25}$ 1.5135 |
| 29 | CH$_3$ | —(CH$_2$)$_3$—C$_6$H$_4$-4-C$_3$H$_7$-i | CH$_3$ | CH$_3$ | H | O | $n_D^{27}$ 1.5246 |
| 30 | CH$_3$ | —(CH$_2$)$_3$—C$_6$H$_4$-4-OC$_4$H$_9$-n | CH$_3$ | CH$_3$ | H | O | $n_D^{24}$ 1.4945 |

TABLE 1-continued $$\text{(I)}$$

Structure (I): A nitrogen bearing $R^1R^2CH$-Z- and $-CR^3R^4-CHR^5(Z)$ substituents, with N-C(=O)-N linked to an imidazole ring.

| Compound No. | $R^1$ | $R^2$ | $R^3$ | $R^4$ | $R^5$ | Z | Physical Property |
|---|---|---|---|---|---|---|---|
| 31 | CH$_3$ | $-(CH_2)_3-$C$_6$H$_4-$OCH$_2$CF$_3$ | CH$_3$ | CH$_3$ | H | O | $n_D^{25}$ 1.5092 |
| 32 | CH$_3$ | $-(CH_2)_3-$C$_6$H$_4-$OC$_3$H$_7$-n | CH$_3$ | CH$_3$ | H | O | $n_D^{24}$ 1.5167 |
| 33 | CH$_3$ | $-(CH_2)_3-$C$_6$H$_4-$OC$_3$H$_7$-i | CH$_3$ | CH$_3$ | H | O | $n_D^{24}$ 1.5038 |
| 34 | CH$_3$ | $-(CH_2)_3-$C$_6$H$_4-$OCH$_3$ | CH$_3$ | CH$_3$ | H | O | $n_D^{24}$ 1.5092 |
| 35 | CH$_3$ | $-(CH_2)_3-$O$-$2,6-Cl$_2$C$_6$H$_3$ | CH$_3$ | CH$_3$ | H | O | |
| 36 | CH$_3$ | $-(CH_2)_3-$O$-$3,4-Cl$_2$C$_6$H$_3$ | CH$_3$ | CH$_3$ | H | O | $n_D^{29}$ 1.5406 |
| 37 | CH$_3$ | $-(CH_2)_5-$O$-$4-ClC$_6$H$_4$ | CH$_3$ | CH$_3$ | H | O | $n_D^{26}$ 1.5293 |
| 38 | CH$_3$ | $-(CH_2)_5-$O$-$(5-CF$_3$-pyridin-2-yl) | CH$_3$ | CH$_3$ | H | O | $n_D^{25}$ 1.5016 |
| 39 | CH$_3$ | $-(CH_2)_2-$O$-$4-ClC$_6$H$_4$ | CH$_3$ | CH$_3$ | H | O | $n_D^{20}$ 1.5003 |
| 40 | CH$_3$ | $-(CH_2)_2-$O$-$4-n-C$_3$H$_7$C$_6$H$_4$ | CH$_3$ | CH$_3$ | H | O | $n_D^{20}$ 1.4943 |

TABLE 1-continued (I)

| Compound No. | R¹ | R² | R³ | R⁴ | R⁵ | Z | Physical Property |
|---|---|---|---|---|---|---|---|
| 41 | $CH_3$ | $-CH_2-O-\underset{}{C_6H_4}-O-C_6H_5$ | $CH_3$ | $CH_3$ | H | O | $n_D^{24}$ 1.5269 |
| 42 | $CH_3$ | $-CH_2-O-C_6H_4-O-$(pyridyl-$CF_3$) | $CH_3$ | $CH_3$ | H | O | $n_D^{24}$ 1.5121 |
| 43 | $CH_3$ | $-CH_2-O-C_6H_4-C_3H_7$-n | $CH_3$ | $CH_3$ | H | O | $n_D^{25}$ 1.5164 |
| 44 | $CH_3$ | $-CH_2-O-C_6H_4-C_4H_9$-n | $CH_3$ | $CH_3$ | H | O | $n_D^{25}$ 1.5021 |
| 45 | $CH_3$ | $-CH_2-O-C_6H_4-C_5H_{11}$-n | $CH_3$ | $CH_3$ | H | O | $n_D^{25}$ 1.5178 |
| 46 | $CH_3$ | $-CH_2-O-C_6H_4-C_6H_{13}$-n | $CH_3$ | $CH_3$ | H | O | $n_D^{25}$ 1.5172 |
| 47 | $CH_3$ | $-CH_2-O-CH_2-C_6H_4-C_4H_9$-n | $CH_3$ | $CH_3$ | H | O | $n_D^{24}$ 1.5054 |
| 48 | $CH_3$ | $-CH_2-O-C_6H_4-OC_3H_7$-n | $CH_3$ | $CH_3$ | H | O | $n_D^{21}$ 1.5102 |
| 49 | $CH_3$ | $-CH_2-O-C_6H_4-OC_4H_9$-n | $CH_3$ | $CH_3$ | H | O | $n_D^{25}$ 1.5016 |
| 50 | $CH_3$ | $-CH_2-O-C_6H_4$(m-$CF_3$) | $CH_3$ | $CH_3$ | H | O | m.p 91~93° C. |
| 51 | $CH_3$ | $-CH_2-S-C_6H_4-Cl$ | $CH_3$ | $CH_3$ | H | O | m.p 123~125° C. |

TABLE 1-continued $$\begin{array}{c} R^1\phantom{xx}Z\phantom{xx}R^5 \\ \diagdown\phantom{x}|\phantom{x}\diagup \\ CH-CH \\ R^2\diagup\phantom{x}|\phantom{x}\diagdown R^4 \\ N\phantom{xx}R^3 \end{array}$$ (I)

| Compound No. | $R^1$ | $R^2$ | $R^3$ | $R^4$ | $R^5$ | Z | Physical Property |
|---|---|---|---|---|---|---|---|
| 52 | $CH_3$ | $-CH_2-S-C_{12}H_{25}$-n | $CH_3$ | $CH_3$ | H | O | $n_D^{25}$ 1.5050 |
| 53 | $CH_3$ | -CH₂CH₂-(2,4-dichlorophenyl) | $CH_3$ | $CH_3$ | H | O | $n_D^{27}$ 1.5263 |
| 54 | $CH_3$ | -CH₂CH₂-(3-chlorophenyl) | $CH_3$ | $CH_3$ | H | O | $n_D^{25}$ 1.5392 |
| 55 | $CH_3$ | -CH₂CH₂-(4-chlorophenyl) | $CH_3$ | $CH_3$ | H | O | $n_D^{25}$ 1.5364 |
| 56 | cyclopropyl (-CH<) | $C_8H_{17}$-n | $CH_3$ | $CH_3$ | H | O | $n_D^{20}$ 1.4892 |
| 57 | cyclopropyl (-CH<) | $C_8H_{17}$-n | H | $CH_3$ | H | O | $n_D^{25}$ 1.4980 |
| 58 | $CH_3$ | -(CH₂)₃-O-(3,4-dichlorophenyl) | H | $C_2H_5$ | H | O | $n_D^{28}$ 1.5457 |
| 59 | $CH_3$ | $C_8H_{17}$-n | H | $C_2H_5$ | H | O | $n_D^{28}$ 1.4876 |
| 60 | $CH_3$ | $C_6H_{13}$-n | H | $C_3H_7$-n | H | O | $n_D^{26}$ 1.4870 |
| 61 | $CH_3$ | $C_6H_{13}$-n | H | phenyl | H | O | $n_D^{28}$ 1.5295 |
| 62 | $CH_3$ | $C_9H_{19}$-n | H | -CH₂-phenyl | H | O | $n_D^{26}$ 1.5135 |
| 63 | $CH_3$ | $C_8H_{17}$-n | { cyclopentylidene (R³ and R⁴ together) } | | H | O | $n_D^{20}$ 1.4901 |

TABLE 1-continued
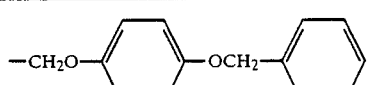
(I)
| Compound No. | R¹ | R² | R³ | R⁴ | R⁵ | Z | Physical Property |
|---|---|---|---|---|---|---|---|
| 64 | CH₃ | −CH₂O−⟨C₆H₄⟩−OCH₂−⟨C₆H₅⟩ |  | | H | O | m.p 146~150° C. |
| 65 | CH₃ | C₆H₁₃-n | 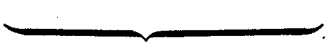 | | H | O | $n_D^{26}$ 1.5164 |
| 66 | 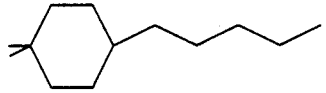 | | CH₃ | CH₃ | H | O | $n_D^{26}$ 1.4836 |
| 67 | 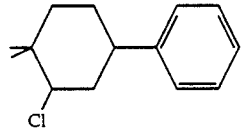 | | CH₃ | CH₃ | H | O | $n_D^{24}$ 1.5489 |
| 68 | 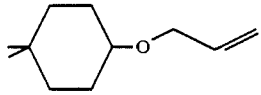 | | CH₃ | CH₃ | H | O | $n_D^{25}$ 1.5104 |
| 69 | 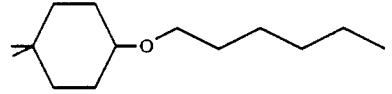 | | CH₃ | CH₃ | H | O | $n_D^{25}$ 1.4970 |
| 70 | 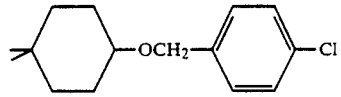 | | CH₃ | CH₃ | H | O | m.p 130~133° C. |
| 71 | 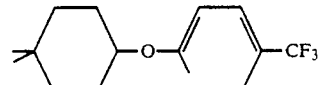 | | CH₃ | CH₃ | H | O | m.p 105~108° C. |
| 72 | 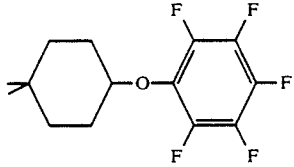 | | CH₃ | CH₃ | H | O | $n_D^{26}$ 1.4967 |
| 73 | 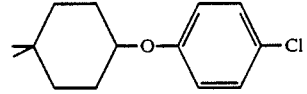 | | CH₃ | CH₃ | H | O | $n_D^{24}$ 1.5152 |

TABLE 1-continued (I)

Structure: R¹R²C(Z)-N(-CHR⁵CR³R⁴-)-C(=O)-N(imidazole)

| Compound No. | R¹ | R² | R³ | R⁴ | R⁵ | Z | Physical Property |
|---|---|---|---|---|---|---|---|
| 74 | | 4,4-dimethylcyclohexyl-S-C₆H₄-Cl | CH₃ | CH₃ | H | O | |
| 75 | | 4,4-dimethylcyclohexyl-S-C₅H₁₁ | CH₃ | CH₃ | H | O | $n_D^{26}$ 1.4872 |
| 76 | | 4,4-dimethylcyclohexyl-OCH₂-C₆H₅ | CH₃ | CH₃ | H | O | $n_D^{20}$ 1.5181 |
| 77 | | 4,4-dimethylcyclohexyl-OCH₂-(2,4-Cl₂-C₆H₃) | CH₃ | CH₃ | H | O | $n_D^{22}$ 1.5439 |
| 78 | | 4,4-dimethylcyclohexyl | H | —CH₂—C₆H₅ | H | O | m.p 93~94° C. |
| 79 | | 4,4-dimethylcyclohexyl-C₆H₅ | H | C₃H₇-n | H | O | $n_D^{26}$ 1.5208 |
| 80 | | 4,4-dimethylcyclohexyl-C₆H₅ | H | CH₃ | C₆H₅ | O | $n_D^{22}$ 1.5525 |
| 81 | | 4,4-dimethylcyclohexyl-C₆H₅ | {1,1-cyclopentyl} | | H | O | m.p 155~158° C. |
| 82 | | 4,4-dimethylcyclohexyl-C₅H₁₁ | {1,1-cyclopentyl} | | H | O | $n_D^{21}$ 1.5116 |
| 83 | CH₃ | —CH₂O—C₆H₅ | H | H | H | S | $n_D^{22}$ 1.5714 |
| 84 | CH₃ | —COOC₂H₅ | H | H | H | S | $n_D^{22}$ 1.5303 |

TABLE 1-continued (I)

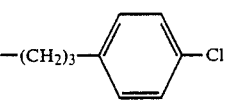

| Compound No. | R¹ | R² | R³ | R⁴ | R⁵ | Z | Physical Property |
|---|---|---|---|---|---|---|---|
| 85 | CH₃ | —(CH₂)₃—C₆H₄—Cl | CH₃ | CH₃ | H | S | |
| 86 | | 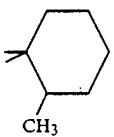 (2-methylcyclohexyl) | H | H | H | S | m.p 90~93° C. |
| 87 | CH₃ | —(CH₂)₃—C₆H₅ | CH₃ | CH₃ | H | O | $n_D^{25}$ 1.5054 |
| 88 | CH₃ | —(CH₂)₂CH(CH₃)C₃H₇ | CH₃ | CH₃ | H | O | $n_D^{26}$ 1.4850 |
| 89 | CH₃ | —CH₂—O—C₆H₃(Cl)—OC₃H₇-n | CH₃ | CH₃ | H | O | $n_D^{24}$ 1.5140 |
| 90 | CH₃ | —(CH₂)₂—O—C₆H₃(Cl)(Cl) | CH₃ | CH₃ | H | O | m.p 78~81° C. |
| 91 | CH₃ | —(CH₂)₂—O—C₆H₄—OC₃H₇-n | CH₃ | CH₃ | H | O | $n_D^{24}$ 1.5011 |
| 92 | CH₃ | C₈H₁₇-n | CH₃ | 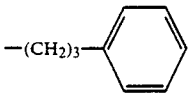 (cyclohexyl group spanning R⁴,R⁵) | | O | $n_D^{25}$ 1.5166 |
| 93 | CH₃ | —CH₂—O—C₆H₄—O—C₅H₁₁-i | CH₃ | CH₃ | H | O | $n_D^{25}$ 1.5144 |
| 94 | CH₃ | —CH₂—O—C₆H₄—O—CH₂—C(Cl)=CHCl | CH₃ | CH₃ | H | O | $n_D^{22}$ 1.5287 |
| 95 | CH₃ | —CH₂—O—C₆H₄—I | CH₃ | CH₃ | H | O | $n_D^{22}$ 1.5419 |

TABLE 1-continued $$\text{(I)}$$

| Compound No. | $R^1$ | $R^2$ | $R^3$ | $R^4$ | $R^5$ | Z | Physical Property |
|---|---|---|---|---|---|---|---|
| 96 | $CH_3$ | $-CH_2-O-$(2,6-diMe-4-Br-phenyl) | $CH_3$ | $CH_3$ | H | O | m.p 124~126° C. |
| 97 | $CH_3$ | $-CH_2-O-$(4-Br-phenyl) | $CH_3$ | $CH_3$ | H | O | $n_D^{28}$ 1.5348 |
| 98 | $CH_3$ | $-CH_2-O-$(4-Cl-phenyl) | $CH_3$ | $CH_3$ | H | O | m.p 68~70° C. |
| 99 | $CH_3$ | $-CH_2-O-$(2-Me-4-Cl-phenyl) | $CH_3$ | $CH_3$ | H | O | m.p 88~90° C. |
| 100 | $CH_3$ | $-CH_2-O-$(3,4-diCl-phenyl) | $CH_3$ | $CH_3$ | H | O | m.p 98~100° C. |
| 101 | $CH_3$ | $-(CH_2)_3-O-$(4-I-phenyl) | $CH_3$ | $CH_3$ | H | O | m.p 81~83° C. |
| 102 | $CH_3$ | $-(CH_2)_3-O-$(4-Br-phenyl) | $CH_3$ | $CH_3$ | H | O | m.p 62~65° C. |
| 103 | $CH_3$ | $-(CH_2)_3-O-$(4-Cl-phenyl) | $CH_3$ | $CH_3$ | H | O | $n_D^{26}$ 1.5215 |
| 104 | $CH_3$ | $-(CH_2)_4-O-$(4-Cl-phenyl) | $CH_3$ | $CH_3$ | H | O | $n_D^{25}$ 1.5020 |
| 105 | $CH_3$ | $-(CH_2)_3-O-$(2,6-diMe-4-Br-phenyl) | $CH_3$ | $CH_3$ | H | O | $0n_D^{25}$ 1.5147 |

TABLE 1-continued

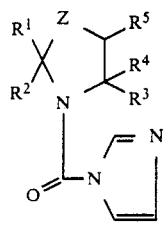
(I)

| Compound No. | R¹ | R² | R³ | R⁴ | R⁵ | Z | Physical Property |
|---|---|---|---|---|---|---|---|
| 106 | CH₃ | —(CH₂)₃—⟨cyclohexyl⟩ | CH₃ | CH₃ | H | O | 0n$_D^{25}$ 1.4988 |
| 107 | CH₃ | —(CH₂)₄—O—⟨C₆H₄⟩—Br | CH₃ | CH₃ | H | O | m.p 72~74° C. |
| 108 | CH₃ | —(CH₂)₄—O—⟨C₆H₄⟩—Cl | CH₃ | CH₃ | H | O | m.p 67~70° C. |
| 109 | | ⟨cyclohexyl-cyclohexyl⟩ | CH₃ | CH₃ | H | O | m.p 115~116° C. |
| 110 | | ⟨cyclohexyl-phenyl⟩ | CH₃ | CH₃ | H | O | m.p 53~56° C. |
| 111 | | ⟨cyclohexyl-C₆H₄-Cl⟩ | CH₃ | CH₃ | H | O | m.p 174~176° C. |
| 112 | | ⟨cyclohexyl-C₆H₄-Br⟩ | CH₃ | CH₃ | H | O | m.p 178~180° C. |
| 113 | | ⟨cyclohexyl-C₆H₄-Cl⟩ | CH₃ | CH₃ | H | O | m.p 177~179° C. |
| 114 | | ⟨cyclohexyl-C₆H₄-Br⟩ | CH₃ | CH₃ | H | O | m.p 100~102° C. |

Of these, particularly preferred are:
2-methyl-2-(p-chlorophenylpropyl)-3-(1-imidazolylcarbonyl)-5,5-dimethyl-1,3-oxazolidine (Compound No. 22) and
2-methyl-2-(p-bromophenylpropyl)-3-(1-imidazolylcarbonyl)-5,5-dimethyl-1,3-oxazolidine (Compound No. 23).

The compound of the formula (I) of the present invention can be prepared by reacting the compound of the formula (III) with an imidazole in the presence of a base as shown in the following reaction scheme.

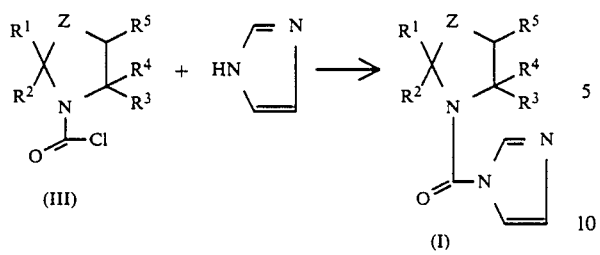

As a reaction medium of the present reaction, there may be used, for example, toluene, acetone, methylethylketone, acetonitrile, dimethylformamide, dimethylsulfoxide and dioxane.

As the base, there may be used, for example, potassium carbonate, sodium carbonate, sodium hydroxide, triethylamine and pyridine.

An amount of the imidazole to be used in the present reaction is preferably 0.5 to 5.0 mole, more preferably 1.0 to 2.0 moles per mole of carbamoyl chloride. A reaction temperature is preferably 20° C. to 150° C., more preferably 50° C. to 100° C. A reaction time is preferably 10 minutes to 8 hours, more preferably 1 to 3 hours. The compound of the formula (III) can be obtained by reacting a secondary amine (IV) with phosgene (V) or trichloromethylchloroformate (VI).

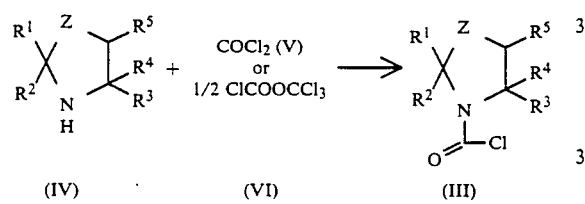

The compounds of the formula (I) show excellent fungicidal effect and also show excellent effects for prophylaxis and therapy of crop diseases caused by plant pathogenic fungus. For example, they show effects particularly to powdery mildew, rust, eyespot, stripe, blast, helminthosporium leaf spot, sheath blight, gray mold, damping-off, leaf spot, black spot, "bakanae" disease and scab. Also, they have excellent effects to diseases caused by bacteria which are resistant to existing agricultural chemicals so that they are advantageous.

When the compounds of the formula (I) of the present invention are used as an agricultural and horticultural fungicide, they can be used in the form of powder, wettable agent, emulsion, granule, fine granule, and other preparations generally employed. A carrier to be used in the present invention may be either a solid or a liquid and not specified to a specific carrier. Suitable carriers which can be used may include solid carriers such as various clays, kaolin, clay, diatomaceous earth, talc and silica; and liquid carriers including those which become a solvent for the compounds of the present invention and those which can disperse or dissolve effective component compounds by an additive even when they are not a solvent. For example, such liquid carriers may include benzene, xylene, toluene, kerosine, alcohols, ketones, dimethylsulfoxide and dimethylformamide. By mixing a suitable surfactant and other auxiliary aids such as a spreading agent and a fixing agent thereto, they can be used as an aqueous solution or an emulsion. Also, the compounds of the present invention may be used by mixing other fungicides, insecticides, herbicides and plant growth controller for saving labor and making prevention effects sure.

EXAMPLES

In the following, Examples of the present invention are shown but the present invention is not limited by these. In the preparation examples, "part(s)" simply mentioned means "part(s) by weight".

EXAMPLE 1

2-Methyl-2-n-hexyl-3-(1-imidazolylcarbonyl)-5,5-dimethyl-1,3-oxazolidine (Compound No. 11)

A mixture comprising 2.6 g (0.01 mole) of 2-methyl-2-n-hexyl-3-chlorocarbonyl-5,5-dimethyl-1,3-oxazolidine, 1.0 g (0.015 mole) of imidazole and 2.1 g (0.015 mole) of potassium carbonate was stirred with 30 ml of dimethylformamide (DMF) as the solvent at 50° C. to 60° C. for one hour. After completion of the reaction, water was added and then the mixture was extracted with toluene. The toluene layer was washed with water, dried and condensed, and then purified by a column chromatography, thereby obtaining 2.7 g of the title compound having pale yellow color.

EXAMPLE 2

2,2-Di-n-heptyl-3-(1-imidazolylcarbonyl)-5,5-dimethyl-1,3-oxazolidine (Compound No. 18)

A mixture comprising 3.0 g (0.01 mole) of 2,2-di-n-heptyl-3-chlorocarbonyl-5,5-dimethyl-1,3-oxazolidine, 1.0 g (0.015 mole) of imidazole and 2.1 g (0.015 mole) of potassium carbonate was stirred with 30 ml of DMF as the solvent at 60° C. to 70° C. for 3 hours. After completion of the reaction, water was added and then the mixture was extracted with toluene. The toluene layer was washed with water, dried and condensed, and then purified by a column chromatography, thereby obtaining 2.8 g of the title compound having pale yellow color.

EXAMPLE 3

Ten (10.00) parts of the compound of Compound No. 13, 69.75 parts of kaolin, 18.00 parts of white carbon, 1.80 parts of NEOPELEX (trade name) and 0.45 part of DEMOL EP (trade name) were uniformly mixed and pulverized to obtain a wettable agent of fine particles. When this material is used as a foliar spreading agent, it is spread to a plant by diluting 200 to 2000-fold. Also, when it is used as a seed disinfectant, it is diluted to 20 to 1000-fold and seed rice are subjected to dipping treatment for 10 minutes to 48 hours.

EXAMPLE 4

Sixty (60) parts of the compound of Compound No. 21, 23 parts of methyl ethyl ketone, 17 parts of polyoxyethylenenonylphenyl ether were mixed and dissolved to obtain an emulsion. When this emulsion is used as a foliar spreading agent, it is spread to a plant by diluting 500 to 4000-fold. Also, when it is used as a seed disinfectant, it is diluted to 10 to 400-fold and seed rice are subjected to dipping treatment for 10 minutes to 48 hours or powdering treatment with an amount of 0.5 to 1% based on the seed rice weight.

EXAMPLE 5

Two (2) parts of the compound of Compound No. 22 and 98 parts of clay were uniformly mixed and pulverized to obtain powder.

EXAMPLE 6

Fifteen (15) parts of water was added to a mixture of 5 parts of the compound of Compound No. 23, 25 parts of bentonite and 67 parts of white carbon, and the mixture was kneaded, and then granulated and dried by a fluidized drier to obtain a granule.

EXAMPLE 7

Control activity test against rice blast (Prevention effect)

Using a plastic pot having a diameter of 5 cm, to a 1.5-leaf stage rice (kind: Nipponbare) land cultivated in a greenhouse was spread each 10 ml of a wettable agent prepared in accordance with Example 3 and diluted to a predetermined concentration, and one day after, a suspension of rice blast spore was inoculated by spraying. After 5 days of the inoculation, number of spots of rice blast per afflicted leaf was examined.

Evaluated results are shown with 6 steps of 5 to 0, and no spot is 5, surface area of afflicted spots being 10 % or less as compared with non-treated district is 4, 20 % or so is 3, 40 % or so is 2, 60 % or so is 1 and whole leaf fallen ill is 0. Examined indexes of chemical damage are 5: remarkably great, 4: great, 3: much, 2: slight, 1: little, and 0: none. The results are shown in Table 2.

TABLE 2

| Compound No. | Concentration (ppm) | Effect | Chemical damage |
| --- | --- | --- | --- |
| 4 | 200 | 5 | 0 |
| 20 | 200 | 5 | 0 |
| 30 | 200 | 5 | 0 |
| 36 | 200 | 5 | 0 |
| 58 | 200 | 5 | 0 |
| 59 | 200 | 5 | 0 |
| 61 | 200 | 5 | 0 |
| 80 | 200 | 5 | 0 |
| Comparative chemical EDDP | 200 | 4 | 0 |
| Non-treated | | 0 | — |

EDDP

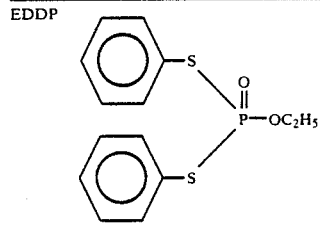

EXAMPLE 8

Control activity test against barley powdery mildew (Prevention effect)

Using a plastic pot having a diameter of 5 cm, to a first-leaf leaf stage barley (kind: Kuromugi) land cultivated in a greenhouse was spread each 10 ml of a wettable agent prepared in accordance with Example 3 and diluted to a predetermined concentration, and one day after, barley powdery mildew spores were inoculated by lightly spraying and shaking spores off on leaves. After 7 days of the inoculation, number of spots of barley powdery mildew per afflicted leaf was examined.

Evaluation and chemical damage are examined in the same index as in Example 7. The results are shown in Table 3.

TABLE 3

| Compound No. | Concentration (ppm) | Effect | Chemical damage |
| --- | --- | --- | --- |
| 4 | 200 | 5 | 0 |
| 14 | 200 | 5 | 0 |
| 18 | 200 | 5 | 0 |
| 22 | 200 | 5 | 0 |
| 23 | 200 | 5 | 0 |
| 24 | 200 | 5 | 0 |
| 25 | 200 | 5 | 0 |
| 26 | 200 | 5 | 0 |
| 29 | 200 | 5 | 0 |
| 37 | 200 | 5 | 0 |
| 42 | 200 | 5 | 0 |
| 49 | 200 | 5 | 0 |
| 63 | 200 | 5 | 0 |
| 66 | 200 | 5 | 0 |
| 67 | 200 | 5 | 0 |
| 71 | 200 | 5 | 0 |
| 73 | 200 | 5 | 0 |
| 82 | 200 | 5 | 0 |
| Comparative chemical Triazimehon | 200 | 5 | 0 |
| Non-treated | | 0 | — |

Triazimehon 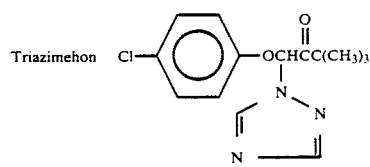

EXAMPLE 9

Control activity test against wheat rust (Prevention effect)

Using a plastic pot having a diameter of 5 cm, to a first-leaf stage wheat (kind: Kobushikomugi) land cultivated in a greenhouse was spread each 10 ml of a wettable agent prepared in accordance with Example 3 and diluted to a predetermined concentration, and one day after, a suspension of wheat rust spore was inoculated by spraying. After 7 days of the inoculation, number of spots of wheat rust per afflicted leaf was examined.

Evaluation and chemical damage are examined in the same index as in Example 7. The results are shown in Table 4.

TABLE 4

| Compound No. | Concentration (ppm) | Effect | Chemical damage |
| --- | --- | --- | --- |
| 14 | 200 | 5 | 0 |
| 15 | 200 | 5 | 0 |
| 21 | 200 | 5 | 0 |
| 22 | 200 | 5 | 0 |
| 23 | 200 | 5 | 0 |
| 24 | 200 | 5 | 0 |
| 25 | 200 | 5 | 0 |
| 26 | 200 | 5 | 0 |
| 27 | 200 | 5 | 0 |
| 36 | 200 | 5 | 0 |
| 49 | 200 | 5 | 0 |
| 53 | 200 | 5 | 0 |
| 54 | 200 | 5 | 0 |
| 58 | 200 | 5 | 0 |
| 63 | 200 | 5 | 0 |
| 66 | 200 | 5 | 0 |
| 67 | 200 | 5 | 0 |
| 68 | 200 | 5 | 0 |
| 69 | 200 | 5 | 0 |
| 71 | 200 | 5 | 0 |

TABLE 4-continued

| Compound No. | Concentration (ppm) | Effect | Chemical damage |
|---|---|---|---|
| 72 | 200 | 5 | 0 |
| 77 | 200 | 5 | 0 |
| 82 | 200 | 5 | 0 |
| Comparative chemical Triazimehon | 200 | 4 | 0 |
| Non-treated | | 0 | — |

EXAMPLE 10

Control Activity test against wheat eyespot (Prevention effect)

Using a plastic pot having a diameter of 5 cm, to a third-leaf stage wheat (kind: Kobushikomugi) land cultivated in a greenhouse was spread each 10 ml of a wettable agent prepared in accordance with Example 3 and diluted to a predetermined concentration, and one day after, a suspension of wheat eyespot spore was inoculated by spraying. After 8 days of the inoculation, number of spots of wheat rust per afflicted leaf was examined.

Evaluation and chemical damage are examined in the same index as in Example 7. The results are shown in Table 5.

TABLE 5

| Compound No. | Concentration (ppm) | Effect | Chemical damage |
|---|---|---|---|
| 22 | 200 | 5 | 0 |
| 23 | 200 | 5 | 0 |
| Comparative chemical Benomil | 200 | 5 | 0 |
| Non-treated | | 0 | — |

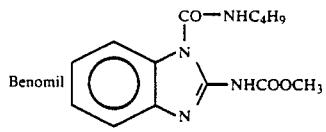

Benomil

EXAMPLE 11

Control Activity test against rice "Bakanae" disease (Prevention effect)

Paddies infected by rice "Bakanae" disease bacteria which are obtained by spraying a condensed spore suspension of rice "Bakanae" disease bacteria to a flowering time rice (kind: Nipponbare) to inoculate are used as test paddies. Disinfection of seeds were carried out by preparing a diluted solution with a predetermined concentration using a wettable agent prepared according to Example 3, and dipping the above test paddies in the diluted solution with a ratio of the above test paddies and the diluted solution (v/v) of 1:1 at 20° C. for 24 hours. The test paddies after disinfection were dipped in water at 20° C. for 3 days, and then germinated at 30° C. for 24 hours and sowed at a soil for cultivation according to the seedlings box seedling culture method in the shape of chicken breast. Thereafter, seedlings were cultivated and controlled in a greenhouse with a glass. Attack of disease was investigated by pulling out all the seedlings of each treated district after 25 days (4-leaf stage) of sewing and the number of seedlings of rice Bakanae disease was countered to obtain a disease attacked seedling ratio (%) whereby prevention value (%) was calculated. Also, in the same standard as in the test example, chemical damage to rice was investigated.

This test was carried out by five ridges per one district and an average seed disinfection ration (%) was measured. The results are as shown in Table 6.

TABLE 6

$$\text{Seeds disinfection ratio (\%)} = \left(1 - \frac{\text{Disease attacked ratio at treated district}}{\text{Disease attacked ratio at non-treated district}}\right) \times 100$$

$$\text{Disease attacked ratio (\%)} = \frac{\text{Number of disease attacked seedlings}}{\text{Number of investigated seedlings}} \times 100$$

| Compound No. | Concentration (ppm) | Seed disinfection ratio (%) | Chemical damage |
|---|---|---|---|
| 13 | 1000 | 100 | 0 |
| 20 | 1000 | 100 | 0 |
| 23 | 1000 | 100 | 0 |
| 26 | 1000 | 100 | 0 |
| 66 | 1000 | 100 | 0 |
| Comparative chemical Benomil | 1000 | 98 | 0 |
| Non-treated | | 0 | — |

We claim:

1. An oxazolidine compound of the formula:

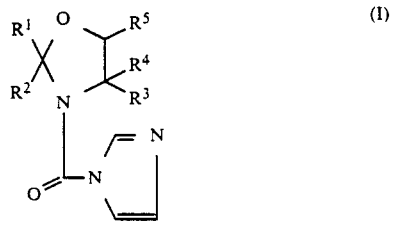

wherein

R¹ represents a hydrogen atom, an alkyl group having 1 to 10 carbon atoms or a cycloalkyl group having 3 to 6 carbon atoms;

R² represents a hydrogen atom, an alkyl group having 1 to 18 carbon atoms, an alkenyl group having 2 to 8 carbon atoms, a lower alkynyl group, an alkoxyalkyl group having 2 to 13 carbon atoms, a lower alkenyloxyalkyl group, an alkylthioalkyl group having 2 to 13 carbon atoms, an alkoxycarbonyl group, a furyl group or a thienyl group, or a phenylalkyl group wherein the alkyl portion has 1 to 5 carbon atoms, a phenoxyalkyl group wherein the alkyl portion has 1 to 5 carbon atoms, a phenylthioalkyl group wherein the alkyl portion has 1 to 5 carbon atoms, a phenylalkyloxyalkyl group wherein the alkyl portion has 1 to 5 carbon atoms, a phenoxyphenoxyalkyl group wherein the alkyl portion has 1 to 5 carbon atoms or a benzyloxyphenoxyalkyl group wherein the alkyl portion has 1 to 5 carbon atoms, those groups having phenyl rings are unsubstituted or substituted by a halogen atom, an alkyl group having 1 to 6 carbon atoms, an alkoxy group having 1 to 4 atoms, a haloalkyl group or a haloalkoxy group; or R¹ and R² may be combined with each other with carbon atoms bonded thereto to form a group represented by the formula:

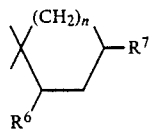

wherein

R$^6$ represents a hydrogen atom, a halogen atom or an alkyl group having 1 to 6 carbon atoms;

R$^7$ represents a hydrogen atom, an alkyl group having 1 to 6 carbon atoms, a lower alkenyl group, an alkoxy group having 1 to 6 carbon atoms, a lower alkenyloxy group or an alkylthio group having 1 to 5 carbon atoms, or a phenyl group, a phenoxy group or a benzyloxy group, those groups having phenyl rings are unsubstituted or substituted by a halogen atom, an alkyl group having 1 to 6 carbon atoms, an alkoxy group having 1 to 4 carbon atoms or a haloalkyl group; n is an integer of 1 to 3;

R$^3$ represents a hydrogen atom or a lower alkyl group;

R$^4$ represents a hydrogen atom, a lower alkyl group, a phenyl group or a benzyl group; or R$^3$ and R$^4$ may be combined with each other with carbon atoms bonded thereto to form a group represented by the formula:

where m is an integer of 4 or 5;

R$^5$ represents a hydrogen atom, a lower alkyl group or a phenyl group.

2. The oxazolidine compound according to claim 1, wherein said R$^1$ is a hydrogen atom or a methyl group.

3. The oxazolidine compound according to claim 1, wherein said R$^2$ is a straight alkyl group having 5 to 12 carbon atoms.

4. The oxazolidine compound according to claim 1, wherein said R$^2$ is a phenoxymethyl group wherein the phenyl group may have a substituent.

5. The oxazolidine compound according to claim 1, wherein said R$^2$ is a phenylalkyl group having a C$_3$ alkyl group and the phenyl group may have a substituent.

6. The oxazolidine compound according to claim 1, wherein said R$^6$ is a chlorine atom or a methyl group.

7. The oxazolidine compound according to claim 1, wherein said R$^1$ is a hydrogen atom or a methyl group, R$^2$ is a straight alkyl group having 5 to 12 carbon atoms, a phenylalkyl group in which the alkyl portion has 1 to 5 carbon atoms, or a phenoxyalkyl group, and the phenyl portion of said groups is unsubstituted or substituted by a halogen atom, an alkyl group having 1 to 6 carbon atoms or an alkoxy group having 1 to 4 carbon atoms; when R$^1$ and R$^2$ and carbon atoms bonded thereto form the group of the formula (II), said R$^6$ is a hydrogen atom or a chlorine atom, said R$^7$ is a hydrogen atom, an alkyl group having 4 to 6 carbon atoms, or a phenyl group which is unsubstituted or substituted by a halogen atom; n is 2; said R$^3$ and R$^4$ are each a methyl group; and R$^5$ is a hydrogen atom.

8. The oxazolidine compound according to claim 1, wherein said compound is 2-methyl-2-(p-chlorophenylpropyl)-3-(1-imidazolylcarbonyl)-4,4-dimethyl-1,3-oxazolidine.

9. An agricultural and horticultural fungicide composition which comprises a fungicidally effective amount of an oxazolidine compound according to claim 1 and an agriculturally and horticulturally acceptable carrier.

10. A method of combatting fungus comprising applying to fungus or to a locus thereof a fungicidally effective amount of an oxazolidine compound according to claim 1.

11. The oxazolidine compound according to claim 1, wherein said compound is 2-methyl-2-(p-bromophenylpropyl)-3-(1-imidazolylcarbonyl)-4,4-dimethyl-1,3-oxazolidine.

12. The fungicide composition according to claim 9, wherein said compound is selected from the group consisting of 2-methyl-2-(p-chlorophenylpropyl)-3-(1-imidazolylcarbonyl)-4,4-dimethyl-1,3-oxazolidine and 2-methyl-2-(p-bromophenylpropyl)-3-(1-imidazolylcarbonyl)-4,4-dimethyl-1,3-oxazolidine.

13. The method according to claim 10, wherein said compound is selected from the group consisting of 2-methyl-2-(p-chlorophenylpropyl)-3-(1-imidazolylcarbonyl)-4,4-dimethyl-1,3-oxazolidine and 2-methyl-2-(p-bromophenylpropyl)-3-(1-imidazolylcarbonyl)-4,4-dimethyl-1,3-oxazolidine.

14. The oxazolidine compound according to claim 1, wherein R$^2$ is 2-propynyl, allyloxyethyl, methoxyethyl, ethoxyethyl, dodecyloxymethyl, Methylthioethyl, dodecylthiomethyl methoxycarbonyl or ethoxycarbonyl, R$^6$ is a methyl group, and R$^7$ is an allyl group, a 2-butenyl group or an allyloxy group.

15. The oxazolidine compound according to claim 1, wherein R$^1$ is a hydrogen atom or a methyl group, R$^2$ is a straight-chain alkyl group having 5 to 12 carbon atoms, a phenoxymethyl group wherein the phenyl portion thereof is unsubstituted or substituted, a phenylalkyl group wherein the alkyl portion thereof is a C$_3$ alkyl group and the phenyl portion thereof is unsubstituted or substituted and R$^6$ is a chlorine atom or a methyl group.

16. The oxazolidine compound according to claim 1, wherein R$^2$ is a selected from the group consisting of a phenylalkyl, phenoxyalkyl, phenylthioalkyl, phenylalkyloxyalkyl and phenoxyphenoxyalkyl, wherein the alkyl portion has 1 to 5 carbon atoms and the phenyl portion is substituted with a substituent selected from the group consisting of chlorine, bromine, fluorine, iodine, methyl, ethyl, propyl, isopropyl, butyl, pentyl, hexyl, methoxy, ethoxy, propyloxy, isopropyloxy, butyloxy, trifluoromethyl and 2,2,2-trifluoroethoxy; and R$^7$ is selected from the group consisting of phenyl, phenoxy and benzyloxy, wherein the phenyl portion thereof is substituted with a substituent selected from the group consisting of chlorine, bromine, fluorine, iodine, methyl, ethyl, propyl, isopropyl, butyl, pentyl, hexyl, methoxy, ethoxy, propyloxy, isopropyloxy, butyloxy and trifluoromethyl.

* * * * *